(12) United States Patent
Fukuzawa

(10) Patent No.: US 8,110,816 B2
(45) Date of Patent: Feb. 7, 2012

(54) FLUORESCENCE DETECTION SYSTEM

(75) Inventor: Takashi Fukuzawa, Tokyo (JP)

(73) Assignee: Nippon Sheet Glass Company, Limited, Tokyo (JP)

( * ) Notice: Subject to any disclaimer, the term of this patent is extended or adjusted under 35 U.S.C. 154(b) by 423 days.

(21) Appl. No.: 12/438,722

(22) PCT Filed: Feb. 20, 2008

(86) PCT No.: PCT/JP2008/053343
§ 371 (c)(1),
(2), (4) Date: Feb. 25, 2009

(87) PCT Pub. No.: WO2008/105435
PCT Pub. Date: Sep. 4, 2008

(65) Prior Publication Data
US 2010/0243915 A1    Sep. 30, 2010

(30) Foreign Application Priority Data

Feb. 28, 2007  (JP) ................. 2007-049272

(51) Int. Cl.
 *G01J 1/58* (2006.01)
(52) U.S. Cl. .................. 250/458.1; 250/461.1
(58) Field of Classification Search ......... 250/458.1, 250/461.1
See application file for complete search history.

(56) References Cited

U.S. PATENT DOCUMENTS

| | | | |
|---|---|---|---|
| 5,142,155 A * | 8/1992 | Mauze et al. | 250/458.1 |
| 5,294,799 A | 3/1994 | Aslund et al. | |
| 5,674,698 A | 10/1997 | Zarling et al. | |
| 6,707,556 B2 * | 3/2004 | Turner et al. | 356/436 |
| 2004/0119976 A1 | 6/2004 | Faupel et al. | |
| 2004/0197267 A1 | 10/2004 | Black et al. | |
| 2006/0109465 A1 | 5/2006 | Fukuzawa et al. | |
| 2006/0238858 A1 | 10/2006 | Kawasaki et al. | |
| 2007/0064228 A1 | 3/2007 | Tartakovsky et al. | |
| 2007/0098594 A1 | 5/2007 | Elkin et al. | |
| 2008/0030718 A1 | 2/2008 | Tamai et al. | |
| 2009/0153852 A1 | 6/2009 | Rensen | |

(Continued)

FOREIGN PATENT DOCUMENTS

JP    06-027110 A    2/1994

(Continued)

OTHER PUBLICATIONS

English Language International Search Report dated Apr. 22, 2008 issued in parent Appln. No. PCT/JP2008/053343.

(Continued)

*Primary Examiner* — David Porta
*Assistant Examiner* — Christine Sung
(74) *Attorney, Agent, or Firm* — Holtz, Holtz, Goodman & Chick, PC

(57) ABSTRACT

A fluorescence detection system capable of detecting fluorescence with a high sensitivity even if a sample generating fluorescence is small in amount includes a light source emitting excitation light, a probe arranged in opposition to a sample unit, an optical multiplexer/demultiplexer, a detector, a first optical fiber connecting the light source to the optical multiplexer/demultiplexer, a second optical fiber connecting the probe to the optical multiplexer/demultiplexer, and a third optical fiber connecting the detector to the optical multiplexer/demultiplexer. An excitation filter, serving as a short-pass filter, is arranged on the first optical fiber and a detection filter serving as a long-pass filter is arranged on the third optical fiber. The optical multiplexer/demultiplexer includes a multiplexing/demultiplexing filter serving as a long-pass filter.

20 Claims, 8 Drawing Sheets

U.S. PATENT DOCUMENTS

2010/0224793 A1  9/2010  Fukuzawa et al.

FOREIGN PATENT DOCUMENTS

| | | |
|---|---|---|
| JP | 8-506419 A | 7/1996 |
| JP | 2003-177096 A | 6/2003 |
| JP | 2005-030830 A | 2/2005 |
| JP | 2006-234794 A | 9/2006 |
| JP | 2006-317282 A | 11/2006 |
| JP | 2007-041510 A | 2/2007 |
| WO | WO 2006/080556 A1 | 8/2006 |

OTHER PUBLICATIONS

U.S. Appl. No. 12/438,536, filed Feb. 23, 2009, "Detection System and Probe Therefor", Takashi Fukuzawa et al.

International Preliminary Report on Patentability and Written Opinion of the International Searching Authority dated Sep. 11, 2009 (7 pages), issued in counterpart International Application No. PCT/JP2008/053343.

* cited by examiner

FLUORESCENCE DETECTION SYSTEM

This application is a U.S. National Phase Application under 35 USC 371 of International Application PCT/JP2008/053343, filed Feb. 20, 2008.

TECHNICAL FIELD

The present invention relates to a fluorescence detection system, and more particularly, to a fluorescence detection system provided with an optical multiplexer/demultiplexer.

BACKGROUND ART

As one example of systems for causing a chemical reaction to occur in a minute space, there has been known a microchemical system. The microchemical system performs mixture, reaction, separation, extraction and detection of a sample in a minute channel formed in a small glass substrate. A sample used in such a microchemical system is generally very small in amount, which requires a high sensitivity detection device for detecting the sample.

When fluorescence is particularly measured using an optical device as a detection device, a fluorescence measurement area is small, so that a higher sensitivity optical device is required. As a method of detecting fluorescence with a high sensitivity, there has been known a laser-induced fluorescence analysis. As an optical device using the laser-induced fluorescence analysis, there is disclosed a fluorescence analysis device including a light source, an optical multiplexer/demultiplexer, a detector and an optical fiber connecting these components together (refer to, for example, Japanese Laid-Open Patent Publication (Kokai) No. 2005-30830).

Incidentally, since the wavelength of excitation light which is used for generating fluorescence varies with a sample to be measured, a laser oscillator is not always used as a light source, for this reason, a light emitting diode (hereinafter, simply referred to as "LED") is generally used as a light source which is capable of outputting a wavelength at which laser does not oscillate.

However, a conventional fluorescence analysis device has a problem that excitation light with which a sample is irradiated from a light source leaks into the detector to increase background at the time of detecting fluorescence, decreasing sensitivity of detecting fluorescence.

As a microchemical system has progressed, a sample to be used becomes smaller in amount, so that the abovementioned problem may become more conspicuous.

The present invention has been made in view of the above problem. The object of the present invention is to provide a fluorescence detection device capable of detecting fluorescence with a high sensitivity even if a sample generating fluorescence is small in amount.

DISCLOSURE OF THE INVENTION

To attain the above object, according to the present invention, there is provided a fluorescence detection system including: a light source adapted to emit excitation light; a probe arranged in opposition to a sample; an optical multiplexer/demultiplexer adapted to multiplex and demultiplex fluorescence generated from the sample irradiated with the excitation light through the probe; a detector adapted to receive the light passing through the optical multiplexer/demultiplexer; and a waveguide adapted to connect the light source to the detector through the optical multiplexer/demultiplexer; wherein the optical multiplexer/demultiplexer includes a first wavelength selection member adapted to transmit only the light whose wavelength is longer than a predetermined first wavelength and reflect the light whose wavelength is shorter than a predetermined second wavelength, and the fluorescence detection system is further comprised of a second wavelength selection member arranged between the light source and the first wavelength selection member on the waveguide and adapted to transmit only the light whose wavelength is shorter than a predetermined third wavelength.

In the present invention, the fluorescence detection system preferably includes a third wavelength selection member arranged between the first wavelength selection member and the detector on the waveguide and adapted to transmit only the light whose wavelength is longer than a predetermined fourth wavelength.

In the present invention, the predetermined fourth wavelength is preferably longer than the predetermined third wavelength by 10 nm or more.

In the present invention, the third wavelength selection member is preferably disposed adjacently to the detector.

In the present invention, the third wavelength selection member is preferably disposed inside the optical multiplexer/demultiplexer.

In the present invention, the predetermined first wavelength is preferably longer than the predetermined third wavelength by 10 nm or more.

In the present invention, the second wavelength selection member is preferably disposed adjacently to the light source.

In order to achieve the above object, in the present invention, there is provided a fluorescence detection system including: a light source adapted to emit excitation light; a probe arranged in opposition to a sample; an optical multiplexer/demultiplexer adapted to multiplex and demultiplex fluorescence generated from the sample irradiated with the excitation light through the probe; a detector adapted to receive the light reflected by the optical multiplexer/demultiplexer; and a waveguide adapted to connect the light source to the detector through the optical multiplexer/demultiplexer; wherein the optical multiplexer/demultiplexer includes a first wavelength selection member adapted to reflect only the light whose wavelength is longer than a predetermined first wavelength and transmit the light whose wavelength is shorter than a predetermined second wavelength, and the fluorescence detection system is further comprised of a second wavelength selection member arranged between the light source and the first wavelength selection member on the waveguide and adapted to transmit only the light whose wavelength is shorter than a predetermined third wavelength and a third wavelength selection member arranged between the first wavelength selection member and the detector on the waveguide and adapted to transmit only the light whose wavelength is longer than a predetermined fourth wavelength.

In the present invention, the predetermined fourth wavelength is preferably longer than the predetermined third wavelength by 10 nm or more.

In the present invention, the second wavelength selection member is preferably disposed adjacently to the light source.

In the present invention, the third wavelength selection member is preferably disposed adjacently to the detector.

In the present invention, the third wavelength selection member is preferably disposed inside the optical multiplexer/demultiplexer.

BEST MODE FOR CARRYING OUT THE INVENTION

Figure 1:
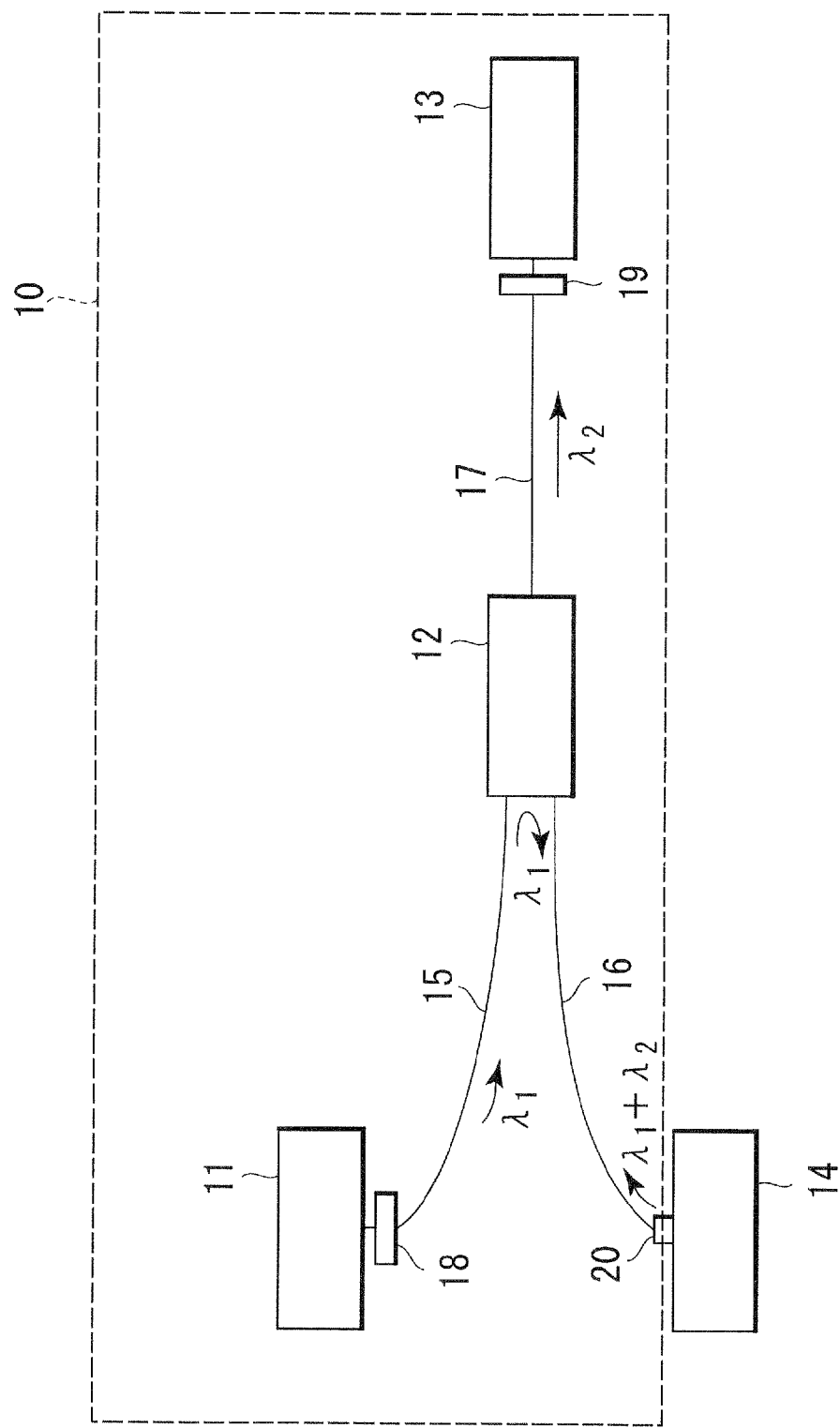
FIG. 1 is a block diagram schematically showing the configuration of a fluorescence detection system according to a first embodiment of the present invention.

The present inventors have dedicated themselves to study to solve the above object and found that the fluorescence detection system described below can lower the background attributed to the excitation light to enable fluorescence to be detected with a high sensitivity even if a sample emitting fluorescence is very small in amount, the fluorescence detection system including: a light source adapted to emit excitation light; a probe arranged in opposition to a sample; an optical multiplexer/demultiplexer adapted to multiplex and demultiplex fluorescence generated from the sample irradiated with the excitation light through the probe; a detector adapted to receive the light passing through the optical multiplexer/demultiplexer; and a waveguide adapted to connect the light source to the detector through the optical multiplexer/demultiplexer; wherein the optical multiplexer/demultiplexer includes a first wavelength selection member adapted to transmit only the light whose wavelength is longer than a predetermined first wavelength and reflect the light whose wavelength is shorter than a predetermined second wavelength, and there is provided a second wavelength selection member arranged between the light source and the first wavelength selection member on the waveguide and adapted to transmit only the light whose wavelength is shorter than a predetermined third wavelength.

The present inventors have also found that the fluorescence detection system described below can lower the background attributed to the excitation light to enable fluorescence to be detected with a high sensitivity even if a sample emitting fluorescence is very small in amount, the fluorescence detection system including: a light source adapted to emit excitation light; a probe arranged in opposition to a sample; an optical multiplexer/demultiplexer adapted to multiplex and demultiplex fluorescence generated from the sample irradiated with the excitation light through the probe; a detector adapted to receive the light reflected by the optical multiplexer/demultiplexer; and a waveguide adapted to connect the light source to the detector through the optical multiplexer/demultiplexer; wherein the optical multiplexer/demultiplexer includes a first wavelength selection member adapted to reflect only the light whose wavelength is longer than a predetermined first wavelength and transmit the light whose wavelength is shorter than a predetermined second wavelength, and there are provided a second wavelength selection member arranged between the light source and the first wavelength selection member on the waveguide and adapted to transmit only the light whose wavelength is shorter than a predetermined third wavelength and a third wavelength selection member arranged between the first wavelength selection member and the detector on the waveguide and adapted to transmit only the light whose wavelength is longer than a predetermined fourth wavelength.

The present invention has been made based on the above knowledge.

A first embodiment of the present invention is described below with reference to the drawings.

First, a fluorescence detection system according to the present embodiment is described.

Figure 2:
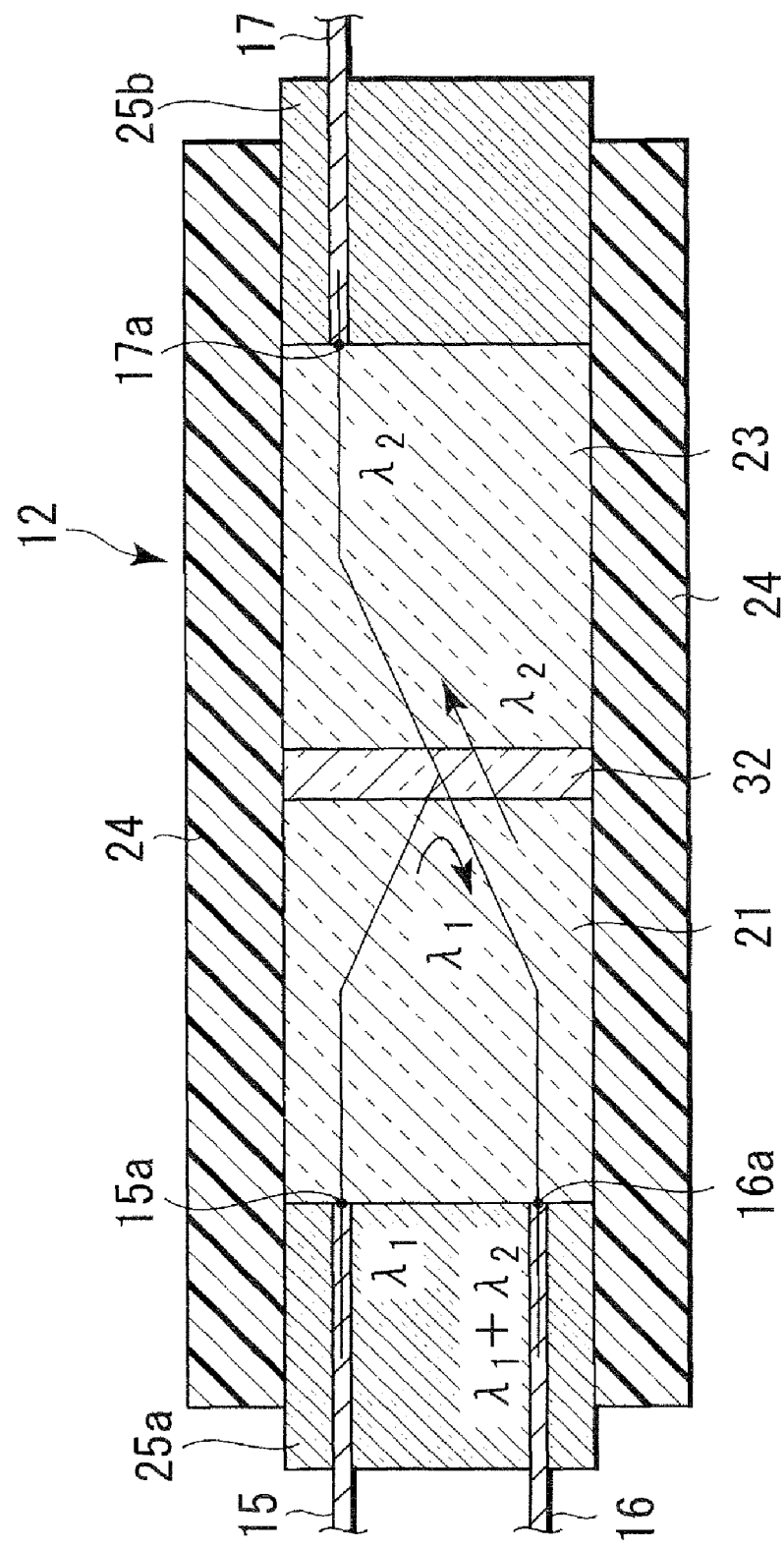
FIG. 2 is a cross sectional view schematically showing the configuration of an optical multiplexer/demultiplexer being a component of the fluorescence detection system in FIG. 1.

FIG. 1 is a block diagram schematically showing the configuration of the fluorescence detection system according to the present embodiment. FIG. 2 is a cross sectional view schematically showing the configuration of an optical multiplexer/demultiplexer being a component of the fluorescence detection system in FIG. 1.

In FIG. 1, the fluorescence detection system 10 includes a light source 11 emitting excitation light (dominant wavelength $\lambda_1$), a probe 20 arranged in opposition to a sample unit 14, an optical multiplexer/demultiplexer 12, a detector 13, an optical fiber 15 (waveguide) connecting the light source 11 to the optical multiplexer/demultiplexer 12, an optical fiber 16 connecting the probe 20 to the optical multiplexer/demultiplexer 12, an optical fiber 17 (waveguide) connecting the detector 13 to the optical multiplexer/demultiplexer 12, an excitation filter 18 (a second wavelength selection member) arranged on the optical fiber 15, and a detection filter 19 (a third wavelength selection member) arranged on the optical fiber 17. A planar waveguide, for example, a ridge waveguide may be used as a waveguide instead of the optical fibers 15 to 17.

The excitation filter 18 is a so-called short-pass filter which transmits light whose wavelength is shorter than a specific cutoff wavelength (for example, 470 nm (a predetermined third wavelength)) and shields light whose wavelength is longer than the cutoff wavelength. The detection filter 19 is a so-called long-pass filter which shields light whose wavelength is shorter than a specific cutoff wavelength (for example, 500 nm (a predetermined fourth wavelength)) and transmits light whose wavelength is longer than the cutoff wavelength.

One end of the probe 20 irradiates the excitation light transmitted through the optical fiber 16 to the sample unit 14 and converges the fluorescence (dominant wavelength $\lambda_2$) generated by the sample unit 14 being irradiated with the transmitted excitation light and the reflected excitation light to transmit them to the optical fiber 16.

In FIG. 2, the optical multiplexer/demultiplexer 12 includes cylindrical rod lenses 21 and 23 and a multiplexing/demultiplexing filter 22 (a first wavelength selection member) interposed between the rod lenses 21 and 23. The optical fibers 15 and 16 whose ends are protected with a capillary 25a are connected to input-output ends 15a and 16a on the face opposite to the face where the rod lens 21 is adjacent to the multiplexing/demultiplexing filter 22. The optical fiber 17 whose end is protected with a capillary 25b is connected to an input-output end 17a on the face opposite to the face where the rod lens 23 is adjacent to the multiplexing/demultiplexing filter 22. A cover 24 is disposed so as to integrally cover the rod lenses 21 and 23, the multiplexing/demultiplexing filter 22 and the capillaries 25a and 25b. The multiplexing/demultiplexing filter 22 is a so-called long-pass filter which reflects light whose wavelength is shorter than a specific cutoff wavelength (for example, 480 nm (a predetermined second wavelength)) and transmits light whose wavelength is longer than the specific cutoff wavelength (for example, 490 nm (a predetermined first wavelength)). Incidentally, the multiplexing/demultiplexing filter 22 may be a bandpass filter which transmits light whose wavelength ranges from, for example, 490 nm to 600 nm.

In FIGS. 1 and 2, only the light whose wavelength is 470 nm or less out of the excitation light emitted from the light source 11 passes through the excitation filter 18 and is transmitted to the input-output end 15a. Light whose wavelength is 480 nm or less out of the excitation light whose wavelength is 470 nm or less transmitted to the input-output end 15a, in other words, all excitation lights transmitted to the input-output end 15a are reflected by the multiplexing/demultiplexing filter 22. The reflected excitation light whose wavelength is 470 nm or less is transmitted to the input-output end 16a and the sample unit 14 is irradiated with the transmitted excitation light through the optical fiber 16 and the probe 20. The fluorescence generated by the sample unit 14 being irradiated with the excitation light and the reflected excitation light whose wavelength is 470 nm or less are transmitted to the input-output end 16a through the probe 20 and the optical fiber 16. Since only the light whose wavelength is 490 nm or more out of the transmitted light passes through the multiplexing/demultiplexing filter 22, the excitation light reflected by the sample unit 14, in other words, all the excitation lights whose wavelength is 470 nm or less are shielded and only the light whose wavelength is 490 nm or more out of the fluorescence passes through the multiplexing/demultiplexing filter 22 and is transmitted to the optical fiber 17 through the input-output end 17a. Only the light whose wavelength is 500 nm or more out of the fluorescence transmitted to the optical fiber 17 passes through the detection filter 19 and reaches the detector 13. The excitation light whose wavelength is 490 nm or less is also irregularly reflected, for example, in the optical multiplexer/demultiplexer 12 and slightly transmitted from the input-output ends 15a or 16a to the input-output end 17a without passing through the multiplexing/demultiplexing filter 22, however, the excitation light making a detour around the multiplexing/demultiplexing filter 22 is shielded with the detection filter 19.

According to the fluorescence detection system 10 in the present embodiment, the optical multiplexer/demultiplexer 12 interposed between the optical fibers 15 and 17 connected to the light source 11 and the detector 13 respectively is provided with the multiplexing/demultiplexing filter 22 forming a long-pass filter with the specific cutoff wavelength and the excitation filter 18 forming a short-pass filter with the specific cutoff wavelength is arranged on the optical fiber 15 connected between the light source 11 and the optical multiplexer/demultiplexer 12. Thereby, the light whose wavelength is longer than the cutoff wavelength of the excitation filter 18 out of the excitation light emitted from the light source 11 and the light whose wavelength is shorter than the cutoff wavelength of the multiplexing/demultiplexing filter 22 do not reach the detector 13, so that background attributed to the excitation light can be lowered, consequently, the fluorescence can be detected with a high sensitivity even if a sample in the sample 14 generating fluorescence is small in amount.

In the fluorescence detection system 10, the detection filter 19 forming a long-pass filter with the specific cutoff wavelength is arranged on the optical fiber 17 connected between the optical multiplexer/demultiplexer 12 and the detector 13. Thereby, the light whose wavelength is shorter than the cutoff wavelength of the detection filter 19 out of the excitation light making a detour around the multiplexing/demultiplexing filter 22 does not reach the detector 13, so that background attributed to the excitation light can be further lowered.

In the present embodiment, the excitation filter 18 may be disposed anywhere as long as it is located on the waveguide between the light source 11 and the multiplexing/demultiplexing filter 22. For example, if the excitation filter 18 is disposed at any position on the optical fiber 15, lenses 41a and 41b are arranged on a line so as to oppose respectively both ends of the excitation filter 18 orthogonal to the waveguide, the optical fibers 15 whose ends are protected with capillaries 42a and 42b are further arranged on a line outside the lenses 41a and 41b and a cover 40 may be provided to integrally cover the excitation filter 18, lenses 41a and 41b and the capillaries 42a and 42b (refer to FIG. 3).

Figure 3:
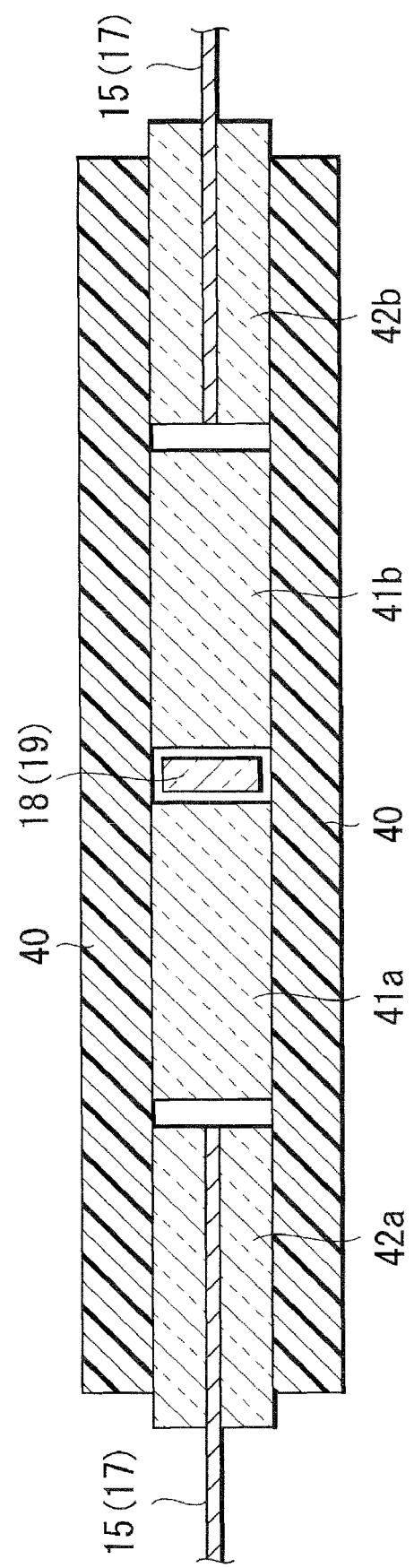
FIG. 3 is a cross sectional view showing the case where an excitation filter or a detection filter illustrated in FIG. 1 is disposed at any position between optical fibers.
Figure 4:
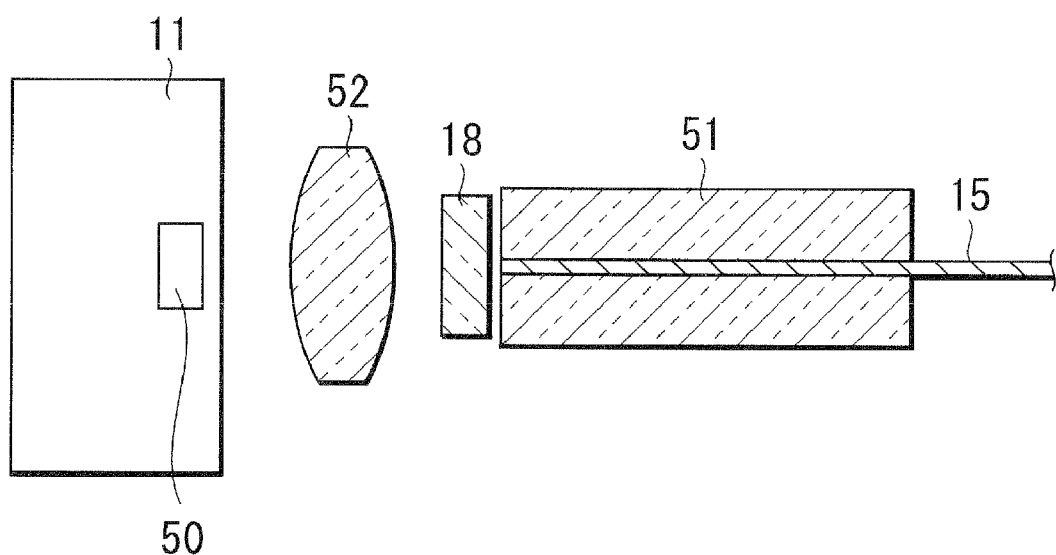
FIG. 4 is a cross sectional view showing the case where the excitation filter in FIG. 1 is disposed adjacently to a light source.

If the excitation filter 18 is disposed adjacently to the light source 11, the excitation filter 18 may be disposed at the end of the optical fiber 15 opposing a condenser lens 52 arranged close to an LED chip 50 in the light source 11 (refer to FIG. 4). In this case, the lenses 41a and 41b in FIG. 3 are not required to enable the number of components to be minimized and the excitation filter 18 to be simply disposed on the fluorescence detection system 10. The excitation filter 18 may be disposed between the condenser lens 52 and the light source 11. If the condenser lens 52 does not intervene therebetween, the excitation filter 18 may be disposed between the LED chip 50 and the optical fiber 15. A luminous body excluding an LED chip may be used as the LED chip 50.

In the present embodiment, the detection filter 19 may be disposed anywhere as long as it is located on the waveguide between the multiplexing/demultiplexing filter 22 and the detector 13. For example, if the detection filter 19 is disposed at any position on the optical fiber 17, the lenses 41a and 41b are arranged on a line so as to oppose respectively both ends of the detection filter 19 orthogonal to the waveguide, the optical fibers 17 whose ends are protected with capillaries 42a and 42b are further arranged on a line outside the lenses 41a and 41b and a cover 40 may be provided to integrally cover the detection filter 19, the lenses 41a and 41b and the capillaries 42a and 42b (refer to FIG. 3).

Figure 5:
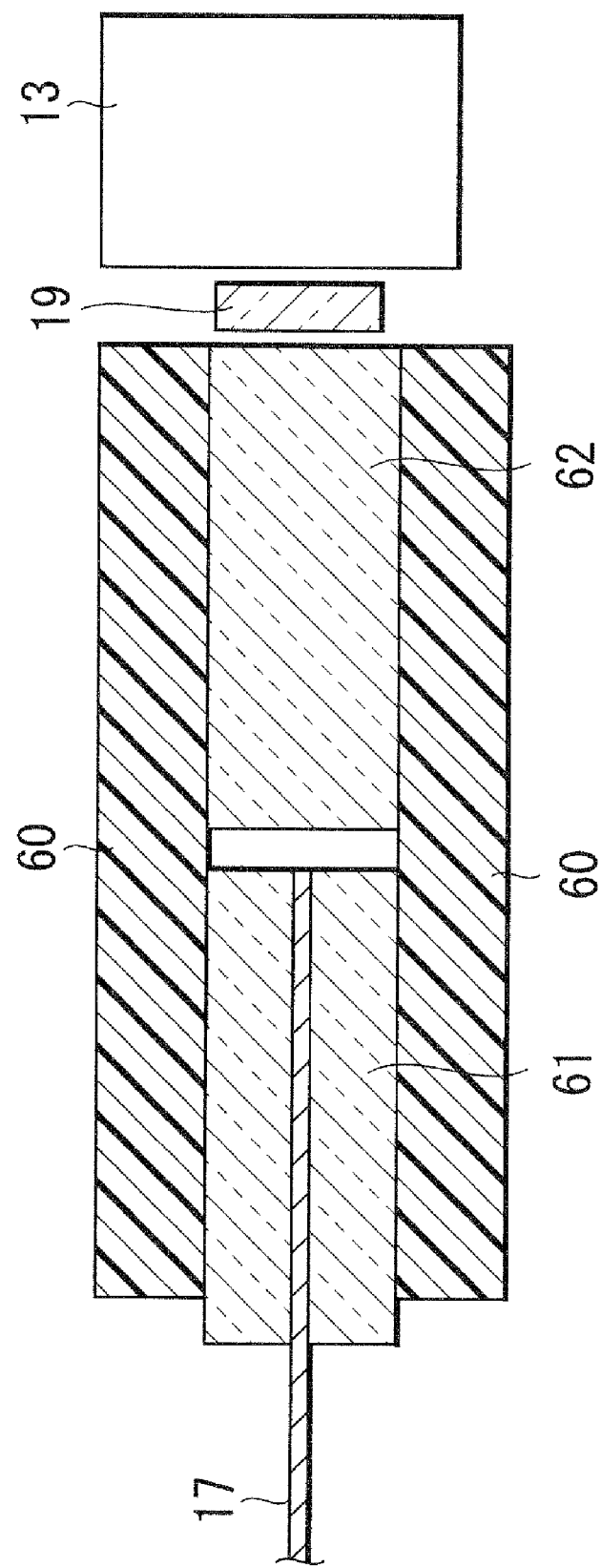
FIG. 5 is a cross sectional view showing the case where the detection filter in FIG. 1 is disposed adjacently to a detector.

If the detection filter 19 is disposed adjacently to the detector 13, a lens 62 is arranged on a line at the end of the optical fiber 17 protected with a capillary 61 and the detection filter 19 may be arranged between the lens 62 and the detector 13 (refer to FIG. 5). In this case, the lenses 41a and 41b are not required to enable the number of components to be minimized and the detection filter 19 to be simply disposed on the fluorescence detection system 10. If the light receiving surface of the detector 13 is wide, the detection filter 19 may be disposed between the optical fiber 17 and the detector 13 without use of the lens 62.

Figure 6:
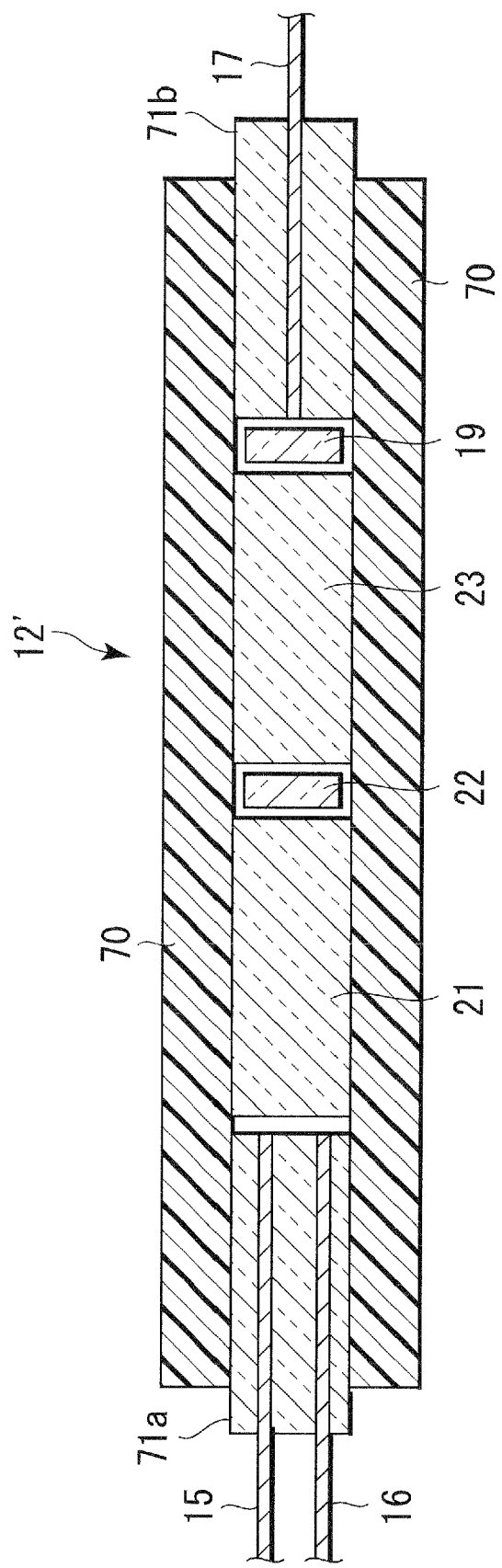
FIG. 6 is a cross sectional view showing the case where the detection filter in FIG. 1 is disposed inside the optical multiplexer/demultiplexer.

If the detection filter 19 is disposed inside the optical multiplexer/demultiplexer 12, the detection filter 19 may be disposed between the rod lens 23 and the optical fiber 17 (refer to FIG. 6). In this case, the detection filter 19 can be simply disposed on the fluorescence detection system 10 without the number of components being increased. Incidentally, the detection filter 19 may be disposed between the multiplexing/demultiplexing filter 22 and the rod lens 23.

In the embodiment of the present invention, the background attributed to the excitation light can be lowered by merely arranging the excitation filter 18 and the fluorescence filter 19 on the fluorescence detection system 10, so that the fluorescence detection system 10 is not complicated.

A fluorescence detection system according to a second embodiment of the present invention is described below.

The present embodiment is basically the same as the foregoing first embodiment in its configuration and function, but it is different therefrom only in the configuration of the optical multiplexer/demultiplexer and a method of connecting the components, so that duplicated description of configuration and function is omitted and different configuration and function are described below.

Figure 7:
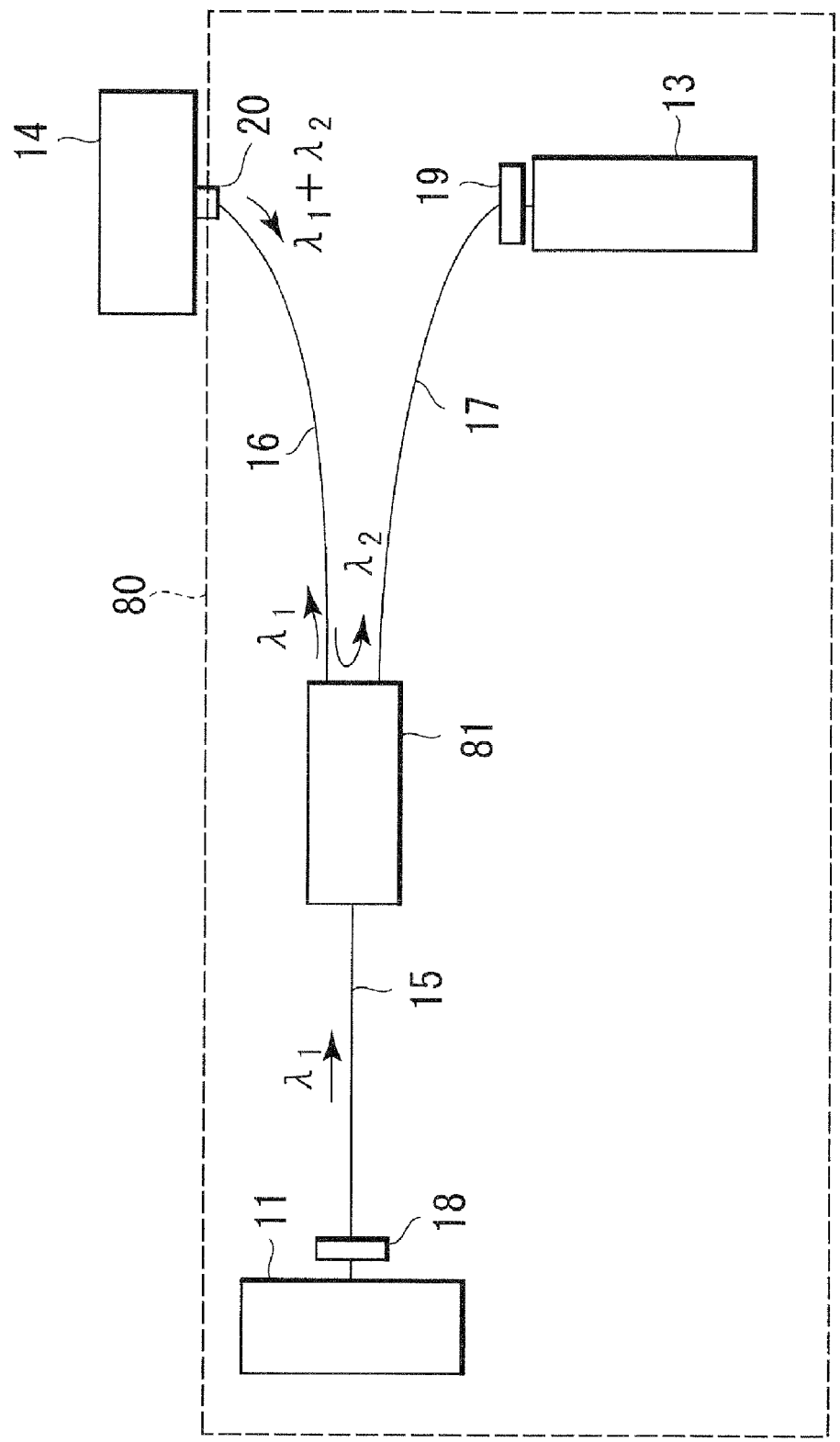
FIG. 7 is a block diagram schematically showing the configuration of a fluorescence detection system according to a second embodiment of the present invention.
Figure 8:
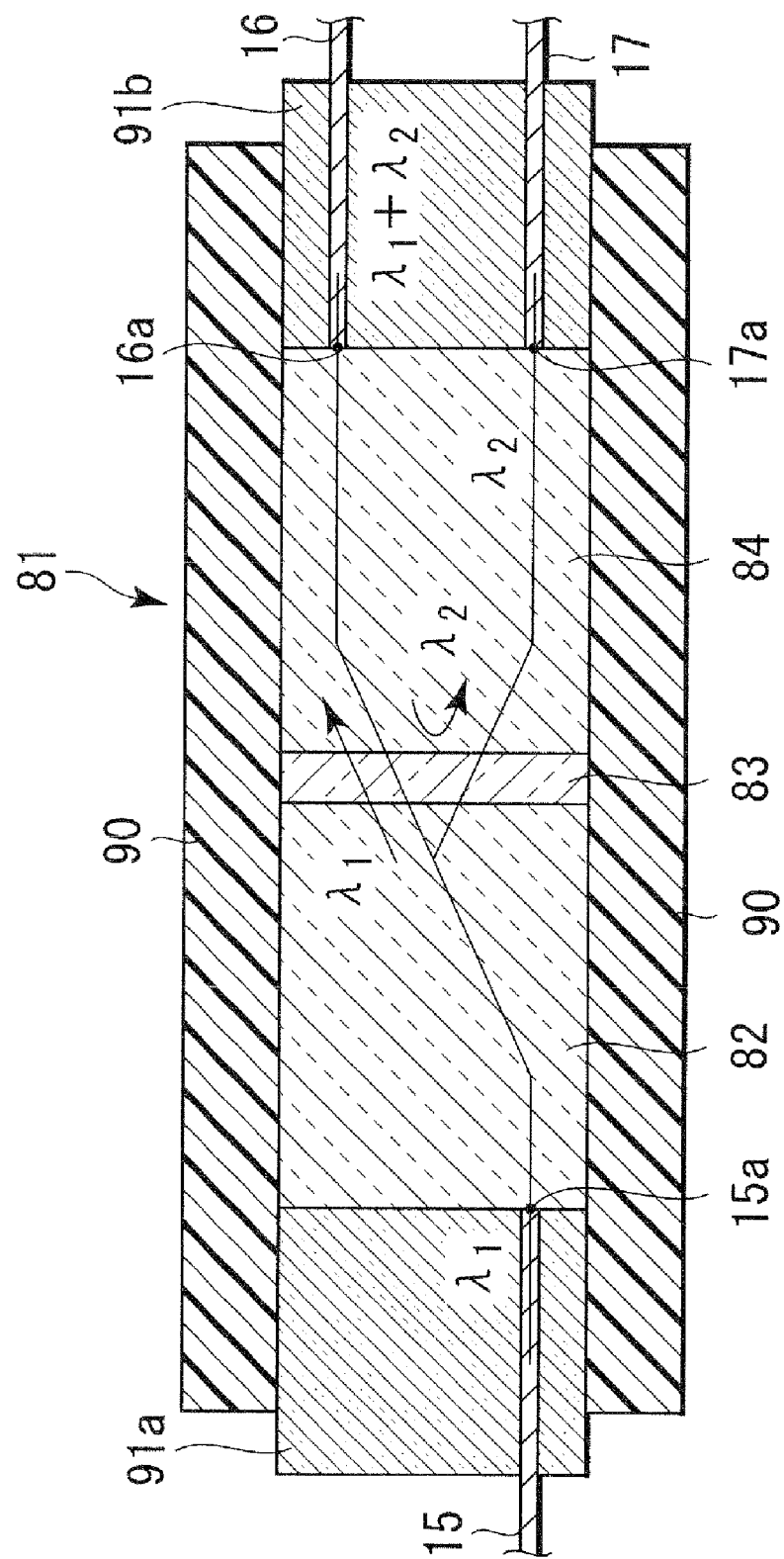
FIG. 8 is a cross sectional view schematically showing the configuration of an optical multiplexer/demultiplexer being a component of the fluorescence detection system in FIG. 7.

FIG. 7 is a block diagram schematically showing the configuration of the fluorescence detection system according to the embodiment of the present invention. FIG. 8 is a cross sectional view schematically showing the configuration of an optical multiplexer/demultiplexer being a component of the fluorescence detection system in FIG. 7.

In FIG. 7, the fluorescence detection system 80 includes a light source 11 emitting excitation light (dominant wavelength $\lambda_1$), a probe 20 arranged in opposition to a sample unit 14, an optical multiplexer/demultiplexer 81, a detector 13, an optical fiber 15 (waveguide) connecting the light source 11 to the optical multiplexer/demultiplexer 81, an optical fiber 16 connecting the probe 20 to the optical multiplexer/demultiplexer 81, an optical fiber 17 (waveguide) connecting the detector 13 to the optical multiplexer/demultiplexer 81, an excitation filter 18 (a second wavelength selection member) arranged on the optical fiber 15 and a detection filter 19 (a third wavelength selection member) arranged on the optical fiber 17.

In FIG. 8, the optical multiplexer/demultiplexer 81 includes cylindrical rod lenses 82 and 84 and a multiplexing/demultiplexing filter 83 (a first wavelength selection member) interposed between the rod lenses 82 and 84. The optical fiber 15 whose end is protected with a capillary 91a is connected to an input-output end 15a on the face opposite to the face where the rod lens 82 is adjacent to the multiplexing/demultiplexing filter 83. The optical fibers 16 and 17 whose ends are protected with a capillary 91b are connected to input-output ends 16a and 17a on the face opposite to the face where the rod lens 84 is adjacent to the multiplexing/demultiplexing filter 83. A cover 90 is disposed so as to integrally cover the rod lenses 82 and 84, the multiplexing/demultiplexing filter 83 and the capillaries 91a and 91b. The multiplexing/demultiplexing filter 83 is a so-called short-pass filter which transmits light whose wavelength is shorter than a specific cutoff wavelength (for example, 480 nm (a predetermined second wavelength)) and reflects light whose wavelength is longer than the specific cutoff wavelength (for example, 490 nm (a predetermined first wavelength)).

In FIGS. 7 and 8, only the light whose wavelength is 470 nm or less out of the excitation light emitted from the light source 11 passes through the excitation filter 18 and is transmitted to the input-output end 15a. Light whose wavelength is 480 nm or less out of the excitation light whose wavelength is 470 nm or less transmitted to the input-output end 15a, in other words, all excitation lights transmitted to the input-output end 15a pass through the multiplexing/demultiplexing filter 83. The passing excitation light whose wavelength is 470 nm or less is transmitted to the input-output end 16a and the sample unit 14 is irradiated with the transmitted excitation light through the optical fiber 16 and the probe 20. The fluorescence (dominant wavelength $\lambda_2$) generated by the sample unit 14 being irradiated with the excitation light and the reflected excitation light whose wavelength is 470 nm or less are transmitted to the input-output end 16a through the probe 20 and the optical fiber 16. Since only the light whose wavelength is 490 nm or more out of the transmitted light is reflected by the multiplexing/demultiplexing filter 83 and the light whose wavelength is 480 nm or less passes through the multiplexing/demultiplexing filter 83, the excitation light reflected by the sample unit 14, in other words, almost all the excitation lights whose wavelength is 470 nm or less pass through the multiplexing/demultiplexing filter 83 and only the light whose wavelength is 490 nm or more out of the fluorescence is reflected by the multiplexing/demultiplexing filter 83 and transmitted to the optical fiber 17 through the input-output end 17a. Only the fluorescence whose wavelength is 500 nm or more passes through the detection filter 19 and reaches the detector 13.

In the case where, for example, the excitation light whose wavelength is 470 nm or less reaches the input-output end 17a through a roundabout path and is slightly transmitted to the input-output end 17a after the excitation light is transmitted to the input-output end 16a through the probe 20 and the optical fiber 16 or, for example, the excitation light whose wavelength is 470 nm or less makes a detour around the multiplexing/demultiplexing filter 83, passes though the optical multiplexer/demultiplexer 81 and is directly transmitted to the input-output end 17a after it is transmitted to the input-output end 15a, the excitation lights reaching the input-output end 17a through a roundabout path and making a detour around the multiplexing/demultiplexing filter 83 are shielded with the detection filter 19.

According to the fluorescence detection system 80 of the present embodiment, the optical multiplexer/demultiplexer 81 interposed between the optical fibers 15 and 17 connected to the light source 11 and the detector 13 respectively is provided with the multiplexing/demultiplexing filter 83 forming a short-pass filter with the specific cutoff wavelength, the excitation filter 18 forming a short-pass filter with the specific cutoff wavelength is arranged on the optical fiber 15 connected between the light source 11 and the optical multiplexer/demultiplexer 81 and the detection filter 19 forming a long-pass filter with the specific cutoff wavelength is arranged on the optical fiber 17 connected between the optical multiplexer/demultiplexer 81 and the detector 13. Thereby, the light whose wavelength is longer than the cutoff wavelength of the excitation filter 18 out of the excitation light emitted from the light source 11 and the light whose wavelength is shorter than the cutoff wavelength of the detection filter 19 do not reach the detector 13, so that background attributed to the excitation light can be lowered, consequently, the fluorescence can be detected with a high sensitivity even if a sample in the sample 14 generating fluorescence is small in amount.

In the present embodiment, the excitation filter 18 may be disposed anywhere as long as it is located on the waveguide between the light source 11 and the multiplexing/demultiplexing filter 83. For example, the excitation filter 18 may be disposed at any position on the optical fiber 15 or disposed adjacent to the light source 11.

In the present embodiment, the detection filter 19 may be disposed anywhere as long as it is located on the waveguide between the multiplexing/demultiplexing filter 83 and the detector 13. For example, the detection filter 19 may be disposed at any position on the optical fiber 17 or disposed adjacent to the detector 13, or disposed inside the optical multiplexer/demultiplexer 81.

In either embodiment, the use of a bandpass filter instead of the long-pass filter or the short-pass filter can also lower the background attributed to the excitation light. Furthermore, a plurality of the excitation filters 18 or the detection filters 19 may be arranged in a plurality of positions. A material forming the optical fibers 15 to 17 may be a transparent solid material capable of transmitting lights. Quartz, glass, plastics or the like can be used as the material. A planar waveguide, for example, a ridge waveguide may be used as a waveguide instead of the optical fibers 15 to 17. In addition, the waveguide may be at least partially formed of a transparent solid material such as glass inside which an optical path is formed.

Next, the examples of the present invention are described below in detail.

First, there is described measurement made using an actual fluorescence detection system.

Example 1

In the fluorescence detection system 10, capillaries (produced by Nippon Electric Glass Co., Ltd.) were fixed to the ends of the optical fibers 15 to 17. In the structure illustrated in FIG. 4, an LED with a center light emitting wavelength of 470 nm (NSPB500S produced by Nichia Corporation) was used as the LED chip 50. An SELFOC (registered trademark) microlens SLW18 (0.4 pitch) (produced by Nippon Sheet Glass Co., Ltd.) was used as the condenser lens 52. The LED chip 50 was coupled to the optical fiber 15 (SI200/250, NA=0.22) through the condenser lens 52 and the excitation filter 18. A short-pass filter with a cutoff wavelength of 490 nm was used as the excitation filter 18.

In the optical multiplexer/demultiplexer 12 illustrated in FIG. 2, an SLW18 (0.23 pitch) (produced by Nippon Sheet Glass Co., Ltd.) was used as the rod lenses 21 and 23 and a long-pass filter which reflects light whose wavelength is 490 nm or less and passes light whose wavelength is 500 nm or more was used as the multiplexing/demultiplexing filter 22. Incidentally, the detection filter 19 was not arranged on the optical fiber 17.

A C5460-01 produced by Hamamatsu Photonics K.K. was used as the detector 13. The SLW18 (0.4 pitch) was used as the probe 20. Aqueous solution in which water and fluorescent dye fluorescein-4-isothiocyanate (hereinafter refer to as "FITC") are prepared to provide concentrations of 0.01 µM, 0.1 µM, 1 µM and 10 µM was used as a sample in the sample unit 14.

In the fluorescence detection system 10, the excitation light was emitted from the light source 11 and the light obtained from the sample unit 14 when the aqueous solutions with the concentrations and the water were irradiated with the excitation light was measured five times to obtain signal values from the detector 13. The averages of the signal values measured five times were calculated and are listed below in a table 1. Incidentally, the signal value is proportional to the quantity of light detected by the detector 13.

TABLE 1

|  | Average | Average differential value | Standard deviation |
|---|---|---|---|
| Water | 116.69 | — | 0.07 |
| 0.01 µM | 116.67 | −0.02 | 0.08 |
| 0.1 µM | 117.30 | 0.61 | 0.10 |
| 1 µM | 185.19 | 68.50 | 0.20 |
| 10 µM | 449.16 | 332.47 | 1.93 |

Example 2

The fluorescence detection system 10 is different from the example 1 and uses an optical multiplexer/demultiplexer 12' illustrated in FIG. 6. The optical multiplexer/demultiplexer 12' used the SLW18 (0.23 pitch) as the rod lenses 21 and 23 and a long-pass filter which reflects light whose wavelength is 490 nm or less and passes light whose wavelength is 500 nm or more as the multiplexing/demultiplexing filter 22. A long-pass filter with a cutoff wavelength of 500 nm used as the detection filter 19 is bonded to the end of a capillary 71b. The detection filter 19 was not arranged on the optical fiber 17. Incidentally, other configurations of the fluorescence detection system 10 in the example 2 are the same as those in the example 1.

As is the case with the example 1, the light obtained from the sample unit 14 when the aqueous solutions with the concentrations and the water were irradiated with the excitation light was measured five times to obtain signal values from the detector 13. The averages of the signal values measured five times were calculated and are listed below in a table 2.

TABLE 2

|  | Average | Average differential value | Standard deviation |
|---|---|---|---|
| Water | 10.41 | — | 0.03 |
| 0.01 µM | 10.43 | 0.02 | 0.04 |
| 0.1 µM | 11.60 | 1.19 | 0.04 |
| 1 µM | 77.88 | 67.47 | 0.36 |
| 10 µM | 748.85 | 738.44 | 1.81 |

Comparative Example 1

The fluorescence detection system 10 is different from the example 1 and the LED chip 50 was coupled to the optical fiber 15 only though the condenser lens 52 and not through the excitation filter 18 in the structure of FIG. 4. The excitation filter 18 was not arranged on the optical fiber 15. The detection filter 19 was not arranged on the optical fiber 17. Incidentally, other configurations of the fluorescence detection system 10 in the comparative example 1 are the same as those in the example 1.

As is the case with the example 1, the light obtained from the sample unit 14 when the aqueous solutions with the concentrations and the water were irradiated with the excitation light was measured five times to obtain signal values from the detector 13. The averages of the signal values measured five times were calculated and are listed below in a table 3.

TABLE 3

|  | Average | Average differential value | Standard deviation |
|---|---|---|---|
| Water | 621.59 | — | 0.06 |
| 0.01 µM | 621.57 | −0.02 | 0.10 |
| 0.1 µM | 621.56 | −0.03 | 0.10 |
| 1 µM | 630.59 | 9.01 | 0.28 |
| 10 µM | 670.42 | 48.84 | 0.10 |

In the tables 1 to 3, the term "average differential value" refers to a difference in which the averages of the signal values obtained when the aqueous solutions with the concentrations were irradiated with the excitation light are subtracted from the averages of the signal values obtained when the water was irradiated with the excitation light. The signal value obtained when the water is irradiated with the excitation light corresponds only to the quantity of light (background) of the excitation light from the light source 11. The signal values obtained when the aqueous solutions with the concentrations are irradiated with the excitation light correspond to the sum total of the quantity of light of the fluorescence from the sample unit 14 and the background. For this reason, "average differential value" corresponds to the quantity of light of the fluorescence from the sample unit 14. If "average differential value" is negative, it means that the background increases, which the fluorescence cannot be detected.

In the tables 1 to 3, the signal values obtained when the waters were irradiated with the excitation light, i.e., the backgrounds were compared with each other. As a result, the background in the example 2 where the excitation filter 18 and the detection filter 19 are arranged on the waveguide connected between the light source 11 and the detector 13 was the smallest of all the examples. The background in the example 1 where only the excitation filter 18 is arranged on the waveguide was the second smallest to the above. The background in the comparative example 1 where neither the excitation filter 18 nor the detection filter 19 are arranged on the waveguide was the largest of all the examples.

In the tables 1 to 3, the concentrations at which a positive average differential value can be obtained, in other words, the concentrations at which the fluorescence can be detected were compared with each other. As a result, the concentration in the example 2 was the lowest (0.01 μM) of all the concentrations. The concentration in the example 1 was the second lowest (0.1 μM) to the above and the concentration in the comparative example 1 was the highest (1 μM).

From these results, it is found that, in the fluorescence detection system 10, at least the excitation filter 18 is arranged on the waveguide connected between the light source 11 and the detector 13 to enable the background to be lowered and the fluorescence to be detected with a high sensitivity even if the concentration of FITC is low (that is to say, a sample emitting the fluorescence is very small in amount).

There is described below simulation carried out using a model of the fluorescence detection system.

A model corresponding to the fluorescence detection systems 10 and 80 was constructed on a computer. Simulation was carried out using the model to confirm a relationship among the presence or absence of the excitation filter 18 and the detection filter 19 and S/B (quantity of light of arrived fluorescence/quantity of light of arrived excitation light (background)) in the detector 13. As the excitation filter 18, the detection filter 19 and the multiplexing/demultiplexing filter 22 (83), there was assumed a filter which is designed so that a transmitting filter (a long-pass filter or a short-pass filter) designed of approximately 100 layers can be provided with a design tilt at a transmission isolation (maximum quantity of light at which light with wavelength in a reflection range is transmitted/quantity of light at which light with wavelength in a reflection range is incident) of −50 dB and at a reflection isolation (maximum quantity of light at which light with wavelength in a transmission range is reflected/quantity of light at which light with wavelength in a transmission range is incident) of −15 dB. In addition, as the LED chip of the light source 11, there was assumed an LED with a center light emitting wavelength of 470 nm. As a sample of the sample unit 14, the FITC was assumed.

Example 3

S/B is calculated in the model (with the detection filter 19 and the excitation filter 18) corresponding to the fluorescence detection system 10, which provides S/B of 89700.

Example 4

As is the case with the example 3, S/B is calculated in the model (with the excitation filter 18) which corresponds to the fluorescence detection system and omits only the detection filter 19 from the fluorescence detection system 10, which provided S/B of 1010.

Comparative Example 2

S/B is calculated in the model (with the detection filter 19) which corresponds to the fluorescence detection system and omits only the excitation filter 18 from the fluorescence detection system 10, which provided S/B of 107, as is the case with the example 3.

Comparative Example 3

As is the case with the example 3, S/B is calculated in the model which corresponds to the fluorescence detection system and omits the excitation filter 18 and the detection filter 19 from the fluorescence detection system 10, which provides S/B of 41.

From the comparison results of S/B in the examples 3 and 4 and the comparative examples 2 and 3, it is found that at least the excitation filter 18 is arranged on the waveguide connected between the light source 11 and the detector 13 to enable S/B to be increased, i.e., the background to be lowered, and the fluorescence to be detected with a high sensitivity.

Example 5

S/B is calculated in the model (with the detection filter 19 and the excitation filter 18) corresponding to the fluorescence detection system 80, which provides S/B of 17500.

Comparative Example 4

As is the case with the example 5, S/B is calculated in the model which corresponds to the fluorescence detection system and omits the excitation filter 18 and the detection filter 19 from the fluorescence detection system 80, which provides S/B of 17.

From the comparison results of S/B in the example 5 and the comparative example 4, it is found that the excitation filter 18 and the detection filter 19 are arranged on the waveguide connected between the light source 11 and the detector 13 to enable S/B to be increased (to 1000 times or more), i.e., the background to be lowered, and the fluorescence to be detected with a high sensitivity.

A model corresponding to the fluorescence detection systems 10 and 30 was constructed on a computer. Simulation was carried out using the model to confirm a relationship between the cutoff wavelength of the excitation filter 18, the detection filter 19 and the multiplexing/demultiplexing filter 22 (83) and S/B in the detector 13. In this case also, as the excitation filter 18, the detection filter 19 and the multiplexing/demultiplexing filter 22 (83), there was assumed a filter which is designed so that a transmitting filter (a long-pass filter or a short-pass filter) designed of approximately 100 layers can be provided with a design tilt at a transmission isolation of −50 dB and at a reflection isolation of −15 dB. In addition, as the LED chip of the light source 11, there was assumed an LED with a center light emitting wavelength of 470 nm. As a sample of the sample unit 14, the FITC was assumed.

Example 6

In the model corresponding to the fluorescence detection system 10, as the excitation filter 18, there was assumed a short-pass filter whose cutoff wavelength is any of 470 nm, 480 nm, 490 nm, 500 nm and 510 nm. As the detection filter 19, there was assumed a long-pass filter whose cutoff wavelength is any of 480 nm, 490 nm, 500 nm, 510 nm, 520 nm and 530 nm. As the multiplexing/demultiplexing filter 22, there was assumed a long-pass filter which reflects light whose wavelength is 480 nm or less and transmits light whose wavelength is 490 nm or more. S/B is calculated as to combinations of cutoff wavelengths of the excitation filter 18 and the detection filter 19 and listed below in the table 4. In the table 4, the first column shows the cutoff wavelength (nm) of the excitation filter 18 and the first row shows the cutoff wavelength (nm) of the detection filter 19.

TABLE 4

|     | 480    | 490    | 500     | 510     | 520     | 530 |
|-----|--------|--------|---------|---------|---------|-----|
| 470 | 133000 | 244000 | 657000  | 1760000 | 3360000 |     |
| 480 | 3060   | 77000  | 1260000 | 3010000 | 5570000 |     |
| 490 | 4.6    | 16.8   | 362000  | 353000  | 291000  |     |
| 500 |        |        | 147     | 182000  | 215000  |     |
| 510 |        |        |         | 336     | 168000  |     |

Example 7

In the model corresponding to the fluorescence detection system 10, S/B is calculated as to combinations of cutoff wavelengths of the excitation filter 18 and the detection filter 19 under the same condition as that in the example 6 except that a long-pass filter which reflects light whose wavelength is 490 nm or less and transmits light whose wavelength is 500 nm or more was assumed as the multiplexing/demultiplexing filter 22, and the calculated S/B is listed below in the table 5. In the table 5, the first column shows the cutoff wavelength (nm) of the excitation filter 18 and the first row shows the cutoff wavelength (nm) of the detection filter 19.

TABLE 5

|     | 480    | 490    | 500     | 510     | 520     | 530      |
|-----|--------|--------|---------|---------|---------|----------|
| 470 | 358000 | 362000 | 660000  | 1910000 | 3620000 |          |
| 480 | 353000 | 594000 | 1090000 | 3150000 | 5930000 |          |
| 490 | 3080   | 4010   | 584000  | 3900000 | 7220000 | 12400000 |
| 500 | 12.4   | 12.4   | 39.8    | 165000  | 755000  |          |
| 510 |        |        |         | 374     | 406000  |          |

Example 8

In the model corresponding to the fluorescence detection system 10, S/B is calculated as to combinations of cutoff wavelengths of the excitation filter 18 and the detection filter 19 under the same condition as that in the example 6 except that a long-pass filter which reflects light whose wavelength is 500 nm or less and transmits light whose wavelength is 510 nm or more was assumed as the multiplexing/demultiplexing filter 22 and a ridge waveguide (NA=0.22) with a core diameter of 200 um instead of the optical fibers 15 to 17 was assumed as a waveguide, and the calculated S/B is listed below in the table 6. In the table 6, the first column shows the cutoff wavelength (nm) of the excitation filter 18 and the first row shows the cutoff wavelength (nm) of the detection filter 19.

TABLE 6

|     | 480    | 490     | 500     | 510     | 520     | 530      |
|-----|--------|---------|---------|---------|---------|----------|
| 470 | 749000 | 760000  | 761000  | 1370000 | 3360000 | 6210000  |
| 480 | 51800  | 1310000 | 1320000 | 2360000 | 5740000 | 10400000 |
| 490 | 12200  | 152000  | 1680000 | 3020000 | 7310000 | 13100000 |
| 500 |        | 13700   | 24000   | 517000  | 7970000 | 14100000 |
| 510 |        |         |         |         | 533000  | 1480000  |

Example 9

In the model corresponding to the fluorescence detection system 80, as the excitation filter 18, there was assumed a short-pass filter whose cutoff wavelength is any of 470 nm, 480 nm, 490 nm, 500 nm and 510 nm, as the detection filter 19, there was assumed a long-pass filter whose cutoff wavelength is any of 480 nm, 490 nm, 500 nm, 510 nm, 520 nm and 530 nm, and as the multiplexing/demultiplexing filter 83, there was assumed a short-pass filter which transmits light whose wavelength is 480 nm or less and reflects light whose wavelength is 490 nm or more. S/B is calculated as to combinations of cutoff wavelengths of the excitation filter 18 and the detection filter 19 and listed below in the table 7. In the table 7, the first column shows the cutoff wavelength (nm) of the excitation filter 18 and the first row shows the cutoff wavelength (nm) of the detection filter 19.

TABLE 7

|     | 480   | 490   | 500   | 510   | 520   | 530   |
|-----|-------|-------|-------|-------|-------|-------|
| 470 | 11000 | 16900 | 38900 | 33600 | 27300 | 19500 |
| 480 | 3.5   | 18800 | 42600 | 36800 | 29900 | 21300 |
| 490 | 1.2   | 1630  | 33900 | 29300 | 23700 | 16900 |

TABLE 7-continued

|     | 480 | 490  | 500   | 510   | 520   | 530   |
|-----|-----|------|-------|-------|-------|-------|
| 500 |     | 1580 | 31500 | 29300 | 23700 | 16900 |
| 510 |     |      |       | 28900 | 23700 | 16900 |

Example 10

In the model corresponding to the fluorescence detection system 80, S/B is calculated as to combinations of cutoff wavelengths of the excitation filter 18 and the detection filter 19 under the same condition as that in the example 9 except that there was assumed a short-pass filter which transmits light whose wavelength is 490 nm or less and reflects light whose wavelength is 500 nm or more as the multiplexing/demultiplexing filter 83, and the calculated S/B is listed below in the table 8. In the table 8, the first column shows the cutoff wavelength (nm) of the excitation filter 18 and the first row shows the cutoff wavelength (nm) of the detection filter 19.

TABLE 8

|  | 480 | 490 | 500 | 510 | 520 | 530 |
| --- | --- | --- | --- | --- | --- | --- |
| 470 | 9460 | 16900 | 18100 | 16200 | 12600 | 9000 |
| 480 | 12 | 14700 | 24800 | 22200 | 17300 | 12300 |
| 490 | 3 | 13 | 24200 | 28500 | 22200 | 15400 |
| 500 | 2 | 4 | 5840 | 27200 | 21200 | 15200 |
| 510 |  |  |  | 36300 | 21200 | 15200 |

Example 11

In the model corresponding to the fluorescence detection system 80, S/B is calculated as to combinations of cutoff wavelengths of the excitation filter 18 and the detection filter 19 under the same condition as that in the example 9 except that a short-pass filter which transmits light whose wavelength is 500 nm or less and reflects light whose wavelength is 510 nm or more was assumed as the multiplexing/demultiplexing filter 83 and a ridge waveguide (NA=0.22) with a core diameter of 200 um instead of the optical fibers 15 to 17 was assumed as the waveguide, and the calculated S/B is listed below in the table 9. In the table 9, the first column shows the cutoff wavelength (nm) of the excitation filter 18 and the first row shows the cutoff wavelength (nm) of the detection filter 19.

TABLE 9

|  | 480 | 490 | 500 | 510 | 520 | 530 |
| --- | --- | --- | --- | --- | --- | --- |
| 470 | 12100 | 37500 | 40500 | 38800 | 30300 | 21600 |
| 480 | 18 | 29100 | 49000 | 46000 | 35900 | 25600 |
| 490 | 4 | 56 | 43500 | 52000 | 40600 | 29000 |
| 500 | 3 | 10 | 59 | 47200 | 42100 | 30100 |
| 510 |  |  |  | 17500 | 41100 | 29400 |

Incidentally, in the tables 4 to 9, the first column shows the cutoff wavelength (nm) of the excitation filter 18 and the first row shows the cutoff wavelength (nm) of the detection filter 19.

From the comparison results of S/B in the examples 6 to 8, it is found that the S/B is increased in the case where the lower limit of the wavelength of light passing through the multiplexing/demultiplexing filter 22 is longer than the cutoff wavelength of the excitation filter 18 by 10 nm or more or the cutoff wavelength of the detection filter 19 is longer than the cutoff wavelength of the excitation filter 18 by 10 nm or more, that is to say, the background attributed to the excitation light is lowered to increase fluorescence detection sensitivity.

Moreover, it is found that the S/B is further increased in the case where the lower limit of the wavelength of light passing through the multiplexing/demultiplexing filter 22 is longer than the cutoff wavelength of the excitation filter 18 by 10 nm or more and the cutoff wavelength of the detection filter 19 is longer than the lower limit of the wavelength of light passing through the multiplexing/demultiplexing filter 22. Still moreover, it is found that the S/B is still further increased in the case where the lower limit of the wavelength of light passing through the multiplexing/demultiplexing filter 22 is longer than the cutoff wavelength of the excitation filter 18 by 10 nm or more and the cutoff wavelength of the detection filter 19 is longer than the cutoff wavelength of the excitation filter 18 by 20 nm or more.

From the comparison results of S/B in the examples 9 to 11, it is found that the cutoff wavelength of the detection filter 19 is longer than the cutoff wavelength of the excitation filter 18 by 10 nm or more, that is to say, the background attributed to the excitation light is lowered to increase fluorescence detection sensitivity.

Moreover, from the results of S/B in the examples 6 to 8 and in the examples 9 to 11, it is found that if using a long-pass filter which reflects the excitation light and transmits the fluorescence as the multiplexing/demultiplexing filter 22, the S/B value can be increased such as to heighten fluorescence detection sensitivity.

INDUSTRIAL APPLICABILITY

According to the present invention, since the optical multiplexer/demultiplexer interposed between waveguides (for example, an optical fiber or a planar waveguide) connected between the light source and the detector is provided with the first wavelength selection member which transmits only the light whose wavelength is longer than a predetermined first wavelength and the second wavelength selection member which transmits only light whose wavelength is shorter than the predetermined third wavelength is arranged between the light source and the first wavelength selection member on the above waveguide, the light whose wavelength is longer than the predetermined third wavelength out of the excitation light emitted from the light source is shielded by the second wavelength selection member and the light whose wavelength is shorter than the predetermined first wavelength out of the excitation light reflected by the first wavelength selection member to the sample and reflected again by the sample to the optical multiplexer/demultiplexer is shielded by the first wavelength selection member. In other words, the light whose wavelength is longer than the predetermined third wavelength and the light whose wavelength is shorter than the predetermined first wavelength out of the excitation light from the light source do not reach the detector. Thereby, the background attributed to the excitation light can be lowered to enable fluorescence to be detected with a high sensitivity even if a sample emitting fluorescence is very small in amount.

Since the third wavelength selection member which transmits only the light whose wavelength is longer than the predetermined fourth wavelength is arranged between the first wavelength selection member and the detector on the waveguide, the light whose wavelength is shorter than the predetermined fourth wavelength out of a slight amount of the excitation light whose wavelength is longer than the predetermined third wavelength and the excitation light whose wavelength is shorter than the predetermined first wavelength which passes through the first wavelength selection member does not reach the detector. Consequently, the background attributed to the excitation light can be further lowered.

The predetermined fourth wavelength is longer than the predetermined third wavelength by 10 nm or more, which allows surely preventing light containing all wavelengths in the excitation light from reaching the detector, thereby the background attributed to the excitation light can be further lowered.

Since the third wavelength selection member is disposed adjacently to the detector, no other components are needed to dispose the third wavelength selection member. Accordingly, the third wavelength selection member can be simply disposed on the fluorescence detection system.

Since the third wavelength selection member is disposed inside the optical multiplexer/demultiplexer, no other components are needed to dispose the third wavelength selection member. Accordingly, the third wavelength selection member can be simply disposed on the fluorescence detection system, in particular, inside the optical multiplexer/demultiplexer.

The predetermined first wavelength is longer than the predetermined third wavelength by 10 nm or more to enable surely preventing light containing all wavelengths in the excitation light from reaching the detector, thereby the background attributed to the excitation light can be further lowered.

Since the second wavelength selection member is disposed adjacently to the light source, no other components are needed to dispose the second wavelength selection member. Accordingly, the second wavelength selection member can be simply disposed on the fluorescence detection system.

According to the present invention, since the optical multiplexer/demultiplexer including the first wavelength selection member is arranged on the waveguide connected between the light source and the detector, the second wavelength selection member which transmits only the light whose wavelength is shorter than the predetermined third wavelength is arranged between the light source and the first wavelength selection member on the waveguide, and the third wavelength selection member which transmits only the light whose wavelength is longer than the predetermined fourth wavelength is arranged between the first wavelength selection member and the detector on the waveguide, the light whose wavelength is longer than the predetermined third wavelength out of the excitation light emitted from the light source is shielded by the second wavelength selection member and the light whose wavelength is shorter than the predetermined fourth wavelength is shielded by the third wavelength selection member out of the excitation light which passes through the optical multiplexer/demultiplexer, reaches the sample, is reflected by the sample to the optical multiplexer/demultiplexer, and then is reflected again by the first wavelength selection member to the detector and the excitation light which makes a detour around the first wavelength selection member to pass though the optical multiplexer/demultiplexer to the detector. In other words, the light whose wavelength is longer than the predetermined third wavelength and the light whose wavelength is shorter than the predetermined fourth wavelength out of the excitation light from the light source do not reach the detector. Thereby, the background attributed to the excitation light can be lowered to enable fluorescence to be detected with a high sensitivity even if a sample emitting fluorescence is very small in amount.

The predetermined fourth wavelength is longer than the predetermined third wavelength by 10 nm or more, which allows surely preventing light containing all wavelengths in the excitation light from reaching the detector, thereby the background attributed to the excitation light can be further lowered.

Since the second wavelength selection member is disposed adjacently to the light source, no other components are needed to dispose the second wavelength selection member. Accordingly, the second wavelength selection member can be simply disposed on the fluorescence detection system.

Since the third wavelength selection member is disposed adjacently to the detector, no other components are needed to dispose the third wavelength selection member. Accordingly, the third wavelength selection member can be simply disposed on the fluorescence detection system.

Since the third wavelength selection member is disposed inside the optical multiplexer/demultiplexer, no other components are needed to dispose the third wavelength selection member. Accordingly, the third wavelength selection member can be simply disposed on the fluorescence detection system and, in particular, inside the optical multiplexer/demultiplexer.

The invention claimed is:

1. A fluorescence detection system comprising:
a light source adapted to emit excitation light; a probe arranged in opposition to a sample;
an optical multiplexer/demultiplexer adapted to multiplex and demultiplex fluorescence generated from the sample irradiated with the excitation light through said probe;
a detector adapted to receive the light passing through said optical multiplexer/demultiplexer; and
a waveguide adapted to connect said light source to said detector through said optical multiplexer/demultiplexer; and wherein:
said optical multiplexer/demultiplexer includes a first wavelength selection member adapted to transmit only the light whose wavelength is longer than a predetermined first wavelength and reflect the light whose wavelength is shorter than a predetermined second wavelength, and
the fluorescence detection system further comprises a second wavelength selection member arranged between said light source and said first wavelength selection member on said waveguide and adapted to transmit only the light whose wavelength is shorter than a predetermined third wavelength.

2. The fluorescence detection system according to claim 1, further comprising a third wavelength selection member arranged between said first wavelength selection member and said detector on said waveguide and adapted to transmit only the light whose wavelength is longer than a predetermined fourth wavelength.

3. The fluorescence detection system according to claim 2, wherein:
the predetermined fourth wavelength is longer than the predetermined third wavelength by 10 nm or more.

4. The fluorescence detection system according to claim 3, wherein:
said third wavelength selection member is disposed adjacently to said detector.

5. The fluorescence detection system according to claim 3, wherein:
said third wavelength selection member is disposed inside said optical multiplexer/demultiplexer.

6. The fluorescence detection system according to claim 3, wherein:
the predetermined first wavelength is longer than the predetermined third wavelength by 10 nm or more.

7. The fluorescence detection system according to claim 2, wherein:
said third wavelength selection member is disposed adjacently to said detector.

8. The fluorescence detection system according to claim 2, wherein:

said third wavelength selection member is disposed inside said optical multiplexer/demultiplexer.

9. The fluorescence detection system according to claim 1, wherein:
the predetermined first wavelength is longer than the predetermined third wavelength by 10 nm or more.

10. The fluorescence detection system according to claim 1, wherein:
said second wavelength selection member is disposed adjacently to said light source.

11. A fluorescence detection system comprising:
a light source adapted to emit excitation light;
a probe arranged in opposition to a sample;
an optical multiplexer/demultiplexer adapted to multiplex and demultiplex fluorescence generated from the sample irradiated with the excitation light through said probe; a detector adapted to receive the light reflected by said optical multiplexer/demultiplexer; and
a waveguide adapted to connect said light source to said detector through said optical multiplexer/demultiplexer; and wherein:
said optical multiplexer/demultiplexer includes a first wavelength selection member adapted to reflect only the light whose wavelength is longer than a predetermined first wavelength and transmit the light whose wavelength is shorter than a predetermined second wavelength, and
the fluorescence detection system further comprises a second wavelength selection member arranged between said light source and said first wavelength selection member on said waveguide and adapted to transmit only the light whose wavelength is shorter than a predetermined third wavelength and a third wavelength selection member arranged between said first wavelength selection member and said detector on said waveguide and adapted to transmit only the light whose wavelength is longer than a predetermined fourth wavelength.

12. The fluorescence detection system according to claim 11, wherein:
the predetermined fourth wavelength is longer than the predetermined third wavelength by 10 nm or more.

13. The fluorescence detection system according to claim 12, wherein:
said second wavelength selection member is disposed adjacently to said light source.

14. The fluorescence detection system according to claim 12, wherein:
said third wavelength selection member is disposed adjacently to said detector.

15. The fluorescence detection system according to claim 12, wherein:
said third wavelength selection member is disposed inside said optical multiplexer/demultiplexer.

16. The fluorescence detection system according to claim 11, wherein:
said second wavelength selection member is disposed adjacently to said light source.

17. The fluorescence detection system according to claim 16, wherein:
said third wavelength selection member is disposed adjacently to said detector.

18. The fluorescence detection system according to claim 16, wherein:
said third wavelength selection member is disposed inside said optical multiplexer/demultiplexer.

19. The fluorescence detection system according to claim 11, wherein:
said third wavelength selection member is disposed adjacently to said detector.

20. The fluorescence detection system according to claim 11, wherein:
said third wavelength selection member is disposed inside said optical multiplexer/demultiplexer.

* * * * *